US011376213B2

(12) United States Patent
Davis et al.

(10) Patent No.: US 11,376,213 B2
(45) Date of Patent: *Jul. 5, 2022

(54) TOPICAL PHARMACEUTICAL FORMULATION

(71) Applicant: Futura Medical Developments Limited, Guildford (GB)

(72) Inventors: Adrian Davis, Guildford (GB); Marc Barry Brown, Shipton under Wychwood (GB)

(73) Assignee: FUTURA MEDICAL DEVELOPMENTS LIMITED, Guildford (GB)

( * ) Notice: Subject to any disclaimer, the term of this patent is extended or adjusted under 35 U.S.C. 154(b) by 166 days.

This patent is subject to a terminal disclaimer.

(21) Appl. No.: 16/308,032

(22) PCT Filed: Jun. 7, 2017

(86) PCT No.: PCT/GB2017/051649
§ 371 (c)(1),
(2) Date: Dec. 7, 2018

(87) PCT Pub. No.: WO2017/212260
PCT Pub. Date: Dec. 14, 2017

(65) Prior Publication Data
US 2019/0216721 A1 Jul. 18, 2019

(30) Foreign Application Priority Data
Jun. 7, 2016 (GB) ..................... 1609968

(51) Int. Cl.
*A61K 9/00* (2006.01)
*A61K 47/10* (2017.01)
*A61K 47/14* (2017.01)
*A61K 31/192* (2006.01)
*A61P 29/00* (2006.01)
*A61K 9/08* (2006.01)

(52) U.S. Cl.
CPC .......... *A61K 9/0014* (2013.01); *A61K 31/192* (2013.01); *A61K 47/10* (2013.01); *A61K 47/14* (2013.01); *A61P 29/00* (2018.01); *A61K 9/08* (2013.01); *A61K 2300/00* (2013.01)

(58) Field of Classification Search
None
See application file for complete search history.

(56) References Cited

U.S. PATENT DOCUMENTS

| 2007/0264295 A1* | 11/2007 | Kantner | A01N 37/18 424/405 |
| 2008/0317684 A1* | 12/2008 | Spann-Wade | A61K 31/185 424/59 |
| 2010/0099767 A1* | 4/2010 | Davis | A61K 9/0014 514/567 |
| 2013/0005816 A1* | 1/2013 | Chen | A61K 9/06 514/570 |

FOREIGN PATENT DOCUMENTS

| WO | 2008/110741 A2 | 9/2008 |
| WO | 2011/070318 A2 | 6/2011 |
| WO | 2012/151427 A1 | 11/2012 |
| WO | 2014/084568 A1 | 6/2014 |
| WO | 2016/132159 A1 | 8/2016 |

OTHER PUBLICATIONS

European Patent Office, International Search Report issued in corresponding Application No. PCT/GB2017/051649, dated Aug. 2, 2017.
Intellectual Property Office, Search Report issued in corresponding Application No. GB 1609968.1, dated Aug. 23, 2016.

* cited by examiner

*Primary Examiner* — Bong-Sook Baek
(74) *Attorney, Agent, or Firm* — Stites & Harbison, PLLC; Terry L. Wright

(57) ABSTRACT

There is described a topical composition for application of an NSAID comprising ibuprofen, the composition comprising a solution or suspension of the NSAID as active ingredient in a residual carrier system comprising a polyhydric alcohol, a glycol ether, an ester of a higher fatty acid and optionally water, the ingredients of the residual carrier system having the following concentrations in percentages by weight: polyhydric alcohol 50-90 glycol ether 7.5-40 ester 0.5-5 water optional in which either the composition or the residual phase is in a single phase under ambient conditions and the maximum water concentration is that above which the composition or the residual phase exhibits signs of inhomogeneity.

19 Claims, 8 Drawing Sheets

TOPICAL PHARMACEUTICAL FORMULATION

FIELD OF THE INVENTION

This invention relates to topical pharmaceutical formulations and, in particular, provides a topical formulation for application of the non-steroidal anti-inflammatory drug (NSAID) ibuprofen for regional transdermal delivery to underlying tissue for analgesic purposes.

BACKGROUND TO THE INVENTION

It is already known to provide formulations containing NSAIDs in the form of gels, creams and sprays intended for topical application for regional delivery to underlying tissues, for the relief of pain and inflammation and to restore mobility. However, some NSAIDs exhibit undesirable side effects either on their own or in interaction with other drugs and, for this reason, there is a continuing need to provide a topical formulation which provides an effective amount for therapeutic activity at the regional tissue target below the application site while at the same time preventing general uptake in the systemic circulation. The objective is to provide local efficacy without the potential for systemic adverse consequences such as gastric, hepatic, renal and other effects. The efficacy of known topical formulations does not compare favourably with that of orally-administered compositions which, however, have general uptake in the systemic circulation.

In designing effective topical formulations, the principal problem to be solved is to enable the active ingredient to penetrate the skin, of which the stratum corneum is, by its nature, an effective barrier medium. For topical NSAID formulations, diclofenac, ketorolac and ketoprofen have been preferred; in particular, the efficacy index for diclofenac (the ratio of its skin penetration to potency) is greater than that for piroxicam by a factor in the order of $10^3$ demonstrating the importance of correct drug selection. Diclofenac and ketoprofen have particularly been preferred on the basis of their more rapid systemic clearance compared with other drugs. Overall, diclofenac has generally been considered to be the preferred NSAID for topical regional application. Trials of a 1% diclofenac sodium gel for use in treating osteoarthritis have demonstrated efficacy and safety, although other diclofenac formulations show efficacy which is inferior to that derived from oral therapy. One currently-available formulation is marketed as "Voltarol Emulgel P", containing 1.16% of diclofenac diethyl ammonium, equivalent to 1 g of diclofenac sodium per 100 g of gel.

In terms of achieving optimum benefit to risk ratio following topical application, it is appropriate to consider the rate of individual drug metabolism in the skin (where rapid metabolism would reduce the potential for local efficacy) and clearance from the systemic circulation (where slow clearance would tend to result in therapeutic levels building up in plasma), which factors vary considerably between different drugs. It has been found from in vivo human studies that topical application of a 4% diclofenac sodium gel achieves skin concentrations which are 2-3 times higher than a therapeutic oral dose of 15 mg diclofenac taken 3 times daily for 3 days, despite having a plasma concentration lowered by approximately 60 times.

In developing topical formulations for enhanced skin penetration of NSAIDS, efforts have hitherto been directed principally at increasing the solubility of the NSAID in the composition as a whole, that is, before application to the skin. More recently, however, formulations have been developed which include a volatile and a non-volatile solvent system so that, on application of the composition to the skin, the volatile solvent evaporates and as a result increases the concentration of the NSAID in the non-volatile solvent. For example, certain currently-available formulations of diclofenac salts are based on the use of a non-volatile solvent such as propylene glycol in combination with a volatile solvent such as ethanol or isopropanol or mixtures thereof. The purpose of the volatile solvent is to increase solubility and also to lead to volume reduction on evaporation in use and thus an increase in diclofenac concentration in the non-volatile, residual phase. Supersaturation of the diclofenac salts in the residual phase may occur but, in any event, it is the degree of saturation in the residual phase which drives the percutaneous penetration process, since diffusion is more a function of chemical potential rather than absolute diclofenac concentration. By way of example, the saturated solubility of diclofenac acid in polyethylene glycol is 11.18% w/w, whereas in propylene glycol the saturated solubility is only 1.16% w/w. Despite this, there is no significant difference between diclofenac flux from these respective systems and indeed, because the saturated solubility of the sodium salt of diclofenac acid in propylene glycol is approximately 50% w/w, it is very difficult to achieve saturation, more especially supersaturation, unless either extremely high concentrations of the salt are used, or an extremely low percentage of the residual phase solvent is used.

Because of the perceived need to optimise the degree of saturation in the residual phase, rather than the absolute concentration, it is important to employ a residual phase solvent or solvent blend which has a relatively low solvating power for the NSAID, such that the saturated concentration is relatively low and in consequence the concentration of the NSAID in the residual phase is more likely to achieve saturation or even super-saturation as the volatile ingredients evaporate, thus optimising NSAID flux and driving skin penetration. It is also desirable for the NSAID to be lipid-soluble, to enable or enhance penetration of the stratum corneum.

WO2008/110741 (Futura Medical Developments Ltd.) describes one such improved topical delivery system in which the NSAID, specifically diclofenac, ketorolac or ketoprofen, preferably diclofenac as diclofenac acid, is dissolved or dispersed in a carrier system comprising a polyhydric alcohol, a glycol ether and an ester of a higher fatty acid, the carrier system being present as a single phase at ambient temperatures and generally including a lower alcohol diluent, water being essentially absent from the carrier system except in impurity amounts.

In the compositions described in WO2008/110741, the polyhydric alcohol, preferably a glycol, renders the active ingredient soluble in the stratum corneum barrier and also increases the solubility of the ester. The ester, preferably a polar lipid, has the effect of increasing diffusivity or transport rate through the stratum corneum barrier. However, the polyhydric alcohol and ester are immiscible in the compositions as described and thus do not form a homogeneous, single-phase carrier system for the active ingredient. The glycol ether is included as a co-solvent and has a polarity between that of the polyhydric alcohol and the ester and is present in an amount at least sufficient to solubilise the other two components and provide a homogeneous, single-phase carrier system. The compositions as described contain (based on the residual phase) at least 2% of ester, in order effectively to increase diffusivity through the stratum corneum and thus requiring concentrations, for example from 30-50% or more, of glycol ether solvent to achieve solubilisation. However, the glycol ether is also an excellent solvent for diclofenac and thus reduces the degree of saturation of diclofenac in the carrier system. For this reason, and also to allay any concerns relating to skin irritation or allergic dermatitis following repeated or prolonged exposure to such compositions, it may be considered desirable to reduce the concentration of glycol ether solvent.

Ibuprofen, isobutylphenylpropionic acid, is an NSAID which is commonly used in formulations for oral administration, especially for treatment of pain arising from menstruation, migraines and rheumatoid arthritis. However, ibuprofen has not hitherto been regarded as a suitable NSAID candidate for use in topical formulations, probably because it has an extremely low aqueous solubility; indeed, those preparations which are currently available and include ibuprofen are not regarded as having acceptable efficacy.

WO2012/151427 (Aponia Laboratories Inc.) relates to transdermal gel compositions containing ibuprofen and is particularly concerned to provide gel formulations which overcome the acknowledged problem of poor skin penetration in humans and animals. The formulations described contain, as excipients, a gelling agent and a solvent, possibly a lower alkyl glycol and a lower alkyl alcohol, and optionally a skin penetration enhancer. Particular emphasis is placed on solving the problem of the poor water solubility of ibuprofen, resulting from its relatively lipophilic nature. To this end, a variety of volatile and non-volatile solvents and other excipients are proposed for use. Exemplary compositions include, inter alia, propylene glycol, isopropyl myristate, hydroxypropyl cellulose, transcutol, isopropyl alcohol, water, dimethyl sulphoxide, oleic acid and/or ethanol. Thus, the teaching of WO2012/151427 is directed to the more traditional approach of providing solvent systems which are intended to improve the solubility of ibuprofen and include one or more skin penetration enhancers to facilitate passage through the stratum corneum.

It has now been realised that the "co-enhancer" technology described in WO2008/110741 may also be applied to ibuprofen as the active ingredient and that water may be included as an optional component, resulting in compositions having enhanced efficacy or other advantages compared with those currently available, such as longer penetration periods so as to enable dosage regimes to be extended.

SUMMARY OF THE INVENTION

In a first aspect, the present invention provides a topical composition for application of an NSAID comprising ibuprofen, the composition comprising a solution or suspension of the NSAID as active ingredient in a residual carrier system comprising a polyhydric alcohol, a glycol ether, an ester of a higher fatty acid and optionally water, the ingredients of the residual carrier system having the following concentrations in percentages by weight:

| | |
|---|---|
| polyhydric alcohol | 50-90 |
| glycol ether | 7.5-40 |
| ester | 0.5-5 |
| water | optional | in which either the composition or the residual phase is in a single phase under ambient conditions and the maximum water concentration is that above which the composition or the residual phase exhibits signs of inhomogeneity.

The skilled person would understand when signs of inhomogeneity are present; such signs include for example haziness or turbidity in an otherwise clear solution, or the presence of an actual precipitate, under ambient conditions (as hereinafter defined).

In the present invention, the NSAID in the composition is ibuprofen, optionally together with one or more other NSAIDs selected from diclofenac, ketorolac, ketoprofen, naproxen and celecoxib. The NSAID may be in salt form or in acid form. The ibuprofen may be present as a racemic mixture of the R and S enantiomers or just as the S enantiomer. The S enantiomer is biologically active but the R enantiomer may be converted in vivo to the S enantiomer via an adenylate conjugate which forms a co-enzyme A thioester which in turn is subject to hydrolysis. Throughout this specification, including the claims, the term "NSAID" is to be understood as meaning ibuprofen and optionally another NSAID selected from those listed above.

Ibuprofen has a pKa of 4.85 at 25° C. and it is therefore preferred for the composition to have a pH of 5.0 or lower, to prevent or at least to discourage ionisation and, thus, to enhance its lipid-solubility. However, for improved stability on storage, a pH closer to 7 (neutral) is desirable and accordingly the inclusion of a neutralising agent to increase the pH may be indicated. Suitable neutralising agents include organic amines such as diethylamine, diethanolamine, triethanolamine, lauryl sulphate, tromethamine, diisopropanolamine and ethylenediamine. Suitable inorganic neutralising agents include sodium hydroxide, potassium hydroxide and liquid ammonia. It is desirable for the neutralising agent to be water-miscible and advantageous if it is also volatile, as hereinafter defined, whereby, in use and on application to the skin, the neutralising agent will evaporate together with the other volatile components so that the pH of the remaining (residual) phase will decrease towards the preferred value for optimum skin penetration. Liquid ammonia can be identified as an inorganic neutralising agent which meets this requirement, whereas diethylamine is an example of an organic neutralising agent which may be used. In this way, the composition, before application to the skin and before evaporation of any of the volatile components, may have a pH of 5 to 8, more preferably, 6 to 8, and even more preferably, 6.5 to 7.5. Further, the composition, after application to the skin and after evaporation of the volatile components, may have a pH of 5 or less, more preferably, 4.5 or less.

Preferably, compositions according to the invention include water. The inclusion of water is advantageous as it prevents or discourages esterification of the carboxylic acid moiety of ibuprofen by polyhydric alcohol, especially in compositions where the pH is less than 5 or more significantly less than 4.5. Put another way, it helps to stabilise the acid form. Water may also act to enhance skin permeability in compositions having a higher pH, around pH 6.5 to 7.5, and may additionally act as a non-solvent to reduce the solubility of the NSAID and, thus, enhance its activity state as the volatile component evaporates. Furthermore, water improves the aesthetic qualities of the resulting gel, making it more acceptable from the user's point of view. However, water also lowers the solubilising power of the composition for the ester component and reduces its saturated solubility, thereby reducing the maximum amount of ester which can be accommodated without compromising a single phase system, so there is a balance to be struck between too little water for the beneficial properties as set out above and too much water resulting in insufficient ester for efficacy. Thus, the amount of water in the composition should, in any event, be lower than the maximum amount which the composition can contain and yet still remain a single-phase system, either in terms of avoiding precipitation of the NSAID and/or separation of the ester component of the system. The skilled person would readily be able to determine the said maximum amount by trial and error, having regard to the current disclosure. However, the maximum concentration of water, as a percentage of the residual carrier system, will preferably be 20% by weight. As to the minimum amount of water, the polyhydric alcohol will naturally contain some water. The minimum amount of added water is that which affects the phase boundary of the ester concentration for a given ratio of polyhydric alcohol:glycol ether but for most purposes the minimum water concentration will be 1% based on the residual phase (as hereinbefore defined). In some embodiments, the minimum water concentration may be 2%, or preferably 2.5%, based on the residual phase. If liquid ammonia is used as the neutralising agent, at a concentration of, for example, 25%, the water content thereof will be included in the total water present in the composition.

In compositions according to the invention, preferred percentage by weight ranges for the ingredients are as follows:

| polyhydric alcohol | 50-80 |
| glycol ether | 15-35 |
| ester | 1-5 |
| water | 2.5-20 |

More preferred percentage by weight ranges for the ingredients are as follows:

| polyhydric alcohol | 55-70 |
| glycol ether | 25-35 |
| ester | 2.5-5 |
| water | 5-15 |

Even more preferred percentage by weight ranges for the ingredients are as follows:

| polyhydric alcohol | 60-65 |
| glycol ether | 25-30 |
| ester | 2.5-4 |
| water | 5-10 |

The composition being a "single phase" means that the components making up the composition form, at equilibrium, a system which is homogeneous thus having uniform physical and chemical characteristics. The components that form the composition are all soluble in the percentages at which they are present to form a homogeneous solution. Preferably, the residual carrier system is present as a single phase at ambient conditions.

In contrast, a two phase system has two distinct phases which have distinct physical and/or chemical characteristics (e.g. water and oil; solid and liquid) and are separated from each other by a discernible phase boundary or are characterised by the presence of a precipitate in a liquid phase.

The compositions according to the invention are single phase at ambient conditions. By "ambient conditions" is meant room temperature under most climatic conditions, say from 5° C. to 40° C., but including the possibility of temperatures down to 0° C. to allow for refrigerator storage. In some embodiments, the composition (and preferably residual carrier system) is single phase at body temperature, for example, about 37° C.

In the compositions according to the invention, as described above, the percentages of the residual carrier system ingredients are relative to the total residual carrier system rather than being relative to the total composition. However, when determining the percentage of each carrier system ingredient and the total residual carrier system (or residual phase), this should be done by analysis of those ingredients within the total formulation "as new", including volatile components, before application in use to the skin. It is to be understood, however, that in use the volatile components will be driven off, thus leaving the non-volatile components as a residual phase.

In the residual phase, where water is present, it is possible that there might be less water than in the total formulation as some water might evaporate. However, for the purposes of determining the total residual carrier system and the percentage of water in the residual carrier system so as to assess whether the ingredient percentages fall within the ranges given above, it is the total formulation "as new" which should be analysed.

In reality, the precise amount of water that is retained in the residual phase will depend on the temperature and relative humidity of the ambient atmosphere. If it is desired to analyse the residual phase as such, the total formulation should be subject to conditions under which the volatile components will evaporate, following which, for the avoidance of doubt, the residual phase should be tested at a temperature of 31° C. and relative humidity of 31.9%. The period of time for which the total formulation is left to allow the volatile components to evaporate should not affect the amount of water retained in the residual phase. However, in practice the total formulation should not be left for longer than 30 minutes. Preferably, the total formulation is left for about 20 minutes before testing the water content of the residual phase. The residual phase should contain the same amount of the other components, i.e. the polyhydric alcohol, the glycol ether and the ester, as in the total formulation, although these can also be easily measured by a person skilled in the art. This method can also be used to determine whether the residual carrier system is single phase.

In this specification, the term "volatile", used to qualify the components which evaporate on application of the composition to the skin, means those components which per se have a half-life at a temperature of 32° C. (the normal temperature of human skin) of one hour or less, preferably 30 minutes or less.

Compositions according to the invention, when applied topically by the fingers to the skin with a rubbing action over an infected or injured target site, form, initially depending upon dose of product per cm$^2$ of skin, a thin film of from 20-50 microns from which the volatile components evaporate to leave a residual phase which becomes absorbed through the stratum corneum to the underlying tissue. The residual phase continuously releases active ingredients over a period of time to provide a sustained dose to the target site. Compositions according to the invention are preferably in the form of a lotion, cream or gel and include further excipient ingredients as required, including preferably a volatile solvent as diluent.

The polyhydric alcohol is preferably a glycol. The glycol may be selected from glycols having from 3-6 carbon atoms including propylene glycol, dipropylene glycol, 1,5 propanediol butylene glycol, hexylene glycol and glycerol, amongst others. In preferred embodiments, the polyhydric alcohol may be propylene glycol.

The ester of a higher fatty acid may be a polar lipid. The polar lipid, as an exemplary sub-class of the esters of a higher fatty acid, may comprise a branched-chain alkyl ester of a $C_{10}$ to $C_{20}$ saturated carboxylic acid such as isopropyl laurate, isopropyl myristate, isopropyl palmitate or propylene glycol monolaurate. Preferably, the polar lipid comprises a branched-chain alkyl ester of a $C_{10}$ to $C_{16}$ saturated carboxylic acid. Further exemplary esters may include glyceryl stearate and triglycerides such as Miglyol 812 or Labrafil MI944CS. In some embodiments, the polar lipid may comprise a branched-chain alkyl ester of a $C_{12}$ to $C_{20}$ saturated carboxylic acid. In preferred embodiments, the ester may be isopropyl myristate.

The glycol ether, referred to for convenience as a co-solvent with the polyhydric alcohol, is preferably a diethylene glycol ether, for example diethylene glycol monoethyl ether (Transcutol®). Other glycol ethers may include phenoxyethanol, diethylene glycol monomethyl ether and Arlamol PS15.

The amount of NSAID, in compositions according to the invention may be up to 10% by weight. In some embodiments, the NSAID may be present at up to 7.5% by weight. In other embodiments, the NSAID may be present at up to 5% by weight or up to 2.5% by weight. Where a salt of the NSAID is used, the said concentrations relate to the free acid. In various embodiments, the NSAID is present at 0.5% to 10% by weight. In a particular embodiment, the NSAID is present at 1% to 10% by weight. In preferred embodiments, the NSAID is present at 0.5% to 6% by weight or at 1% to 5% by weight. The percentages referred to above are with respect to the total formulation.

In preferred embodiments, where water is present, the composition comprises between 5% and 9% water by weight, between 6% and 8% water by weight, or about 7% water by weight, being expressed as percentages by weight based on the residual carrier system. However, in some compositions according to the invention, higher amounts of water, for example 12%, 15% or higher up to around 20%, may be preferred for reasons of preserving or enhancing the aesthetic qualities or the skin tolerance of the composition. As mentioned previously, the upper limit on water content is defined by maintenance of a single phase system.

The ester preferably ranges from 2.7% to 4.5%, more preferably from 3% to 4%, more preferably still from 3.25% to 3.75%, for example about 3.5%, all concentrations being expressed as percentages by weight based on the residual carrier system.

The glycol ether preferably ranges from 15% to 35%, more preferably from 25% to 30% by weight, for example about 28%, by weight based on the residual carrier system.

The polyhydric alcohol preferably ranges from 55% to 80%, more preferably 60% to 65% by weight, for example about 62%, based by weight on the residual carrier system.

Within the above concentration ranges for the components of the carrier system, the water may be present in a ratio of from 5% to 12.5% of the polyhydric alcohol and the ratio of polyhydric alcohol (including water) to glycol ether is preferably in the range 80:20 to 60:40, more preferably 75:25 to 65:35.

Preferably, compositions according to the invention also include a volatile solvent which, in conjunction with the other components of the carrier system, solubilises the active ingredient at saturation levels and evaporates on application to the skin, thus driving the active ingredient towards or to supersaturation in the residual phase, resulting in enhanced flux of active ingredient. Volatile organic solvents suitable for use in the present invention includes lower alcohols containing up to 5 carbon atoms, for example ethanol or isopropyl alcohol (IPA), and liquid-phase ketones. In some embodiments, the volatile solvent may be ethanol and/or isopropyl alcohol (IPA). The volatile solvent may be in a range of 15 to 50% by weight relative to the total weight of the composition. In some embodiments, the volatile solvent may be in a range of 15 to 40% by weight relative to the total weight of the composition. Alternatively, the volatile solvent may be in a range of 15 to 30% by weight relative to the total weight of the composition, in a range of 20 to 28% by weight, in a range of 20 to 27% by weight, or in a range of 20 to 26% by weight based on the total composition. The presence of water in the composition may enable the concentration of organic solvent to be reduced, thus (for example in the case of IPA) improving the skin tolerance of the composition.

By "liquid phase" in relation to ketones in this specification is meant a ketone having the formula R—C(O)—R which is liquid at ambient temperatures and in which the R groups are the same or different and are alkyl groups optionally substituted by OH, halogen, acetyl (whereby the ketone is acetyl acetone), or other group which, by virtue of its chemical nature or its effect on electron distribution, enhances the solubility properties of the solvent or its rate of evaporation in use. Thus, although higher homologues than acetone, for example, methylethylketone or diethylketone, may be used, acetone is considered to be especially useful because of its ability to undergo keto-enol tautomerism, where the enol form is more stable. Indeed, acetyl acetone, also capable of undergoing keto-enol tautomerism, exists substantially as the enol form.

Optionally, compositions according to the invention contain a polyhydric alcohol including three or more hydroxyl groups as part of the residual carrier system, as a non-solvent to reduce the solubility of the NSAID and, thus, to enhance its activity state. Exemplary polyhydric alcohols for this purpose include glycerol and sorbitol, preferably glycerol, at a concentration up to 15% by weight of the total formulation. In some embodiments, this polyhydric alcohol may be present at up to 12.5% by weight. In other embodiments, the polyhydric alcohol may be present at up to 10% by weight, up to 7.5% by weight, for example, about 5% by weight. Preferably, the amount of polyhydric alcohol (e.g. glycerol) is 0.5% to 15% by weight of the total composition. In some embodiments, the amount of polyhydric alcohol (e.g. glycerol) is 1% to 15% by weight of the total composition. In other embodiments, the amount of polyhydric alcohol (e.g. glycerol) is 2% to 15% by weight of the total composition. The upper limits described above for the polyhydric alcohol also apply to the ranges. Therefore, for example, the polyhydric alcohol may be present at 1% to 10% or 1% to 7.5% by weight of the total composition. This component, if present, is in addition to the polyhydric alcohol required as an essential ingredient of the carrier system of compositions according to the invention. In order to maintain a single phase, the amount of polyhydric alcohol needs to be adjusted accordingly.

To enhance stability in a supersaturated residual phase which may have a tendency to instability, it is desirable that the composition also includes an antinucleating agent, to discourage recrystallisation of the drug component, which would lead to lower amounts being available for uptake. Nucleation and recrystallisation are likely to be most problematical where higher degrees of supersaturation are experienced in the residual phase. Antinucleating agents may comprise antinucleant polymers, including cellulose, for example hydroxypropyl cellulose, hydroxypropylmethyl cellulose, ethyl cellulose, hydroxypropylmethyl cellulose acetate succinate, and hydroxypropylmethyl cellulose phthalate; pyrrolidones, for example polyvinylpyrrolidone and polyvinylpyrrolidone vinyl acetate copolymer; and acrylates/methacrylates. Such antinucleating agents may be present at between 1% and 5%, between 1% and 3%, or about 2% by weight, based on the total composition.

Compositions according to the invention may also include sensory signals, for example menthol and/or eucalyptus oil. Almost immediately after application these agents give a cooling sensation to the skin which is appreciated by users and heralds the onset of pain relief. Alternatively, the sensory signals may be an agent which gives a warming sensation to the skin after application of the agent.

Other optional ingredients, as known in the art, may be added to compositions according to the invention for formulation purposes depending on the intended mode of application, including for example thickening or gelling agents such as hydroxypropyl cellulose or hydroxyethyl cellulose, anti-tack agents such as dimethicone silicone fluid, for example having a viscosity of 0.65CST, and propellants for spray formulations. Further optional ingredients may be added to the compositions according to the invention, such as a fragrance.

The presence of water at concentrations greater than 10% by weight may be advantageous in that such concentrations would enable the use, as gelling agent, of hydroxyethyl cellulose in place of hydroxypropyl cellulose. Hydroxyethyl cellulose imparts to the composition enhanced aesthetic properties, making it more acceptable to the user, and is more robust in that phase separation even at such higher water concentrations is prevented.

Rather than specifying the percentages of the carrier system components that form the residual phase in terms of the weight of the carrier system components, the percentages of the components can be specified relative to the total formulation. These percentages relate to the composition as a whole, i.e. before it has been applied to the skin and before any of the volatile components have evaporated.

Therefore, in total formulation terms, compositions according to the invention may comprise, in percentages by weight and apart from the NSAID:

| | |
|---|---|
| polyhydric alcohol | 20-60 |
| glycol ether | 5-30 |
| ester | 0.3-3 |
| water (optional) | 2.5-15 |
| lower alcohol | 20-50 |

In preferred embodiments, in total formulation terms, compositions according to the invention may comprise, in percentages by weight:

| | |
|---|---|
| NSAID | 0.5-5% |
| polyhydric alcohol | 25-50 |
| glycol ether | 10-25 |
| ester | 1-2.5 |
| water (optional) | 2.5-10 |
| lower alcohol | 20-50 |

In addition, the various compositions described above may comprise dimethicone (0.5-2.5% or 1-2%) and/or hydroxypropyl cellulose (1-3% or 1.5-2.5%).

DETAILED DESCRIPTION OF THE INVENTION

Embodiments of the invention will now be described by way of example with reference to the accompanying drawings, of which.

Figure 1:
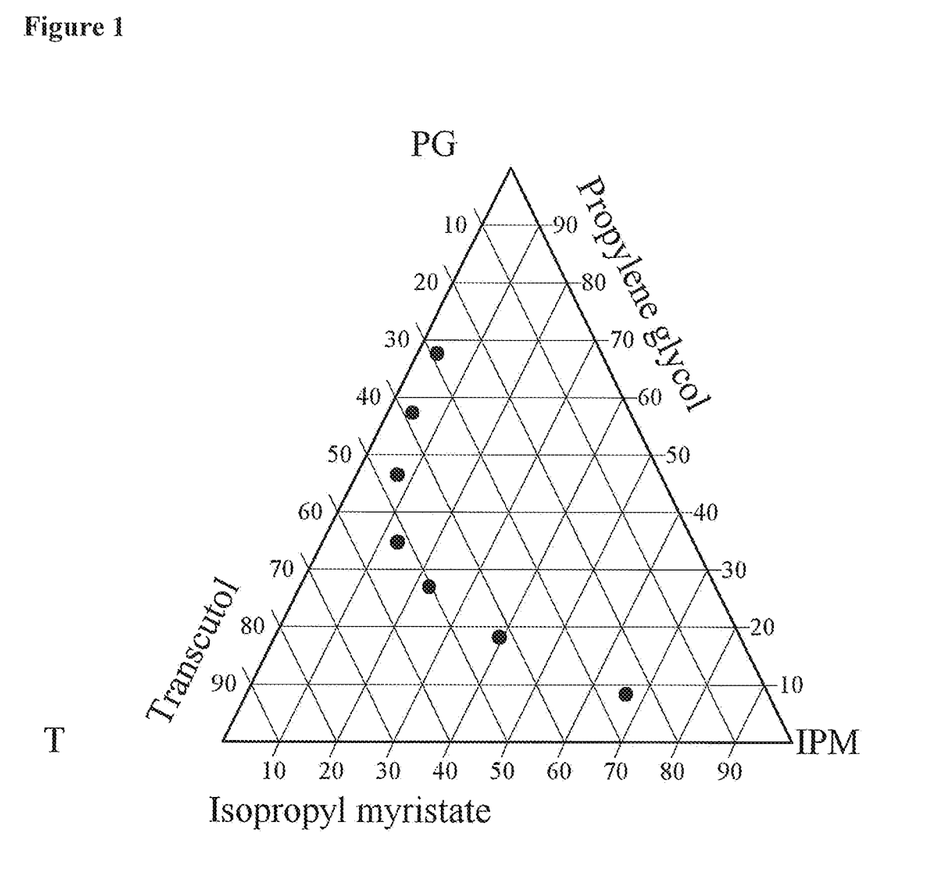
FIG. 1 is a phase diagram for comparative purposes of a carrier system comprising propylene glycol (PG), Transcutol (T) and isopropyl myristate (IPM), but no added water.

Referring to FIG. 1, the phase diagram shows the effect of addition of isopropyl myristate, to mixtures of propylene glycol and a co-solvent (Transcutol). The phase boundary is represented by the curve joining the points of the single-phase system where the polar lipid is at unit, saturated thermodynamic activity. The area to the left of the phase boundary relates to single-phase systems and, as can be seen on following the phase boundary curve from 70:30 glycol: Transcutol to 10:90 glycol:Transcutol, the polar lipid concentration can be increased while saturation is maintained. For each ratio of glycol and Transcutol, a plotted point represents the maximum amount of isopropyl myristate that the system can tolerate whilst still remaining single phase.

The different carrier systems which from the phase diagram are seen to be possible in terms of enabling inclusion of the polar lipid at saturation amounts have different solubilising powers for diclofenac.

Figure 2:
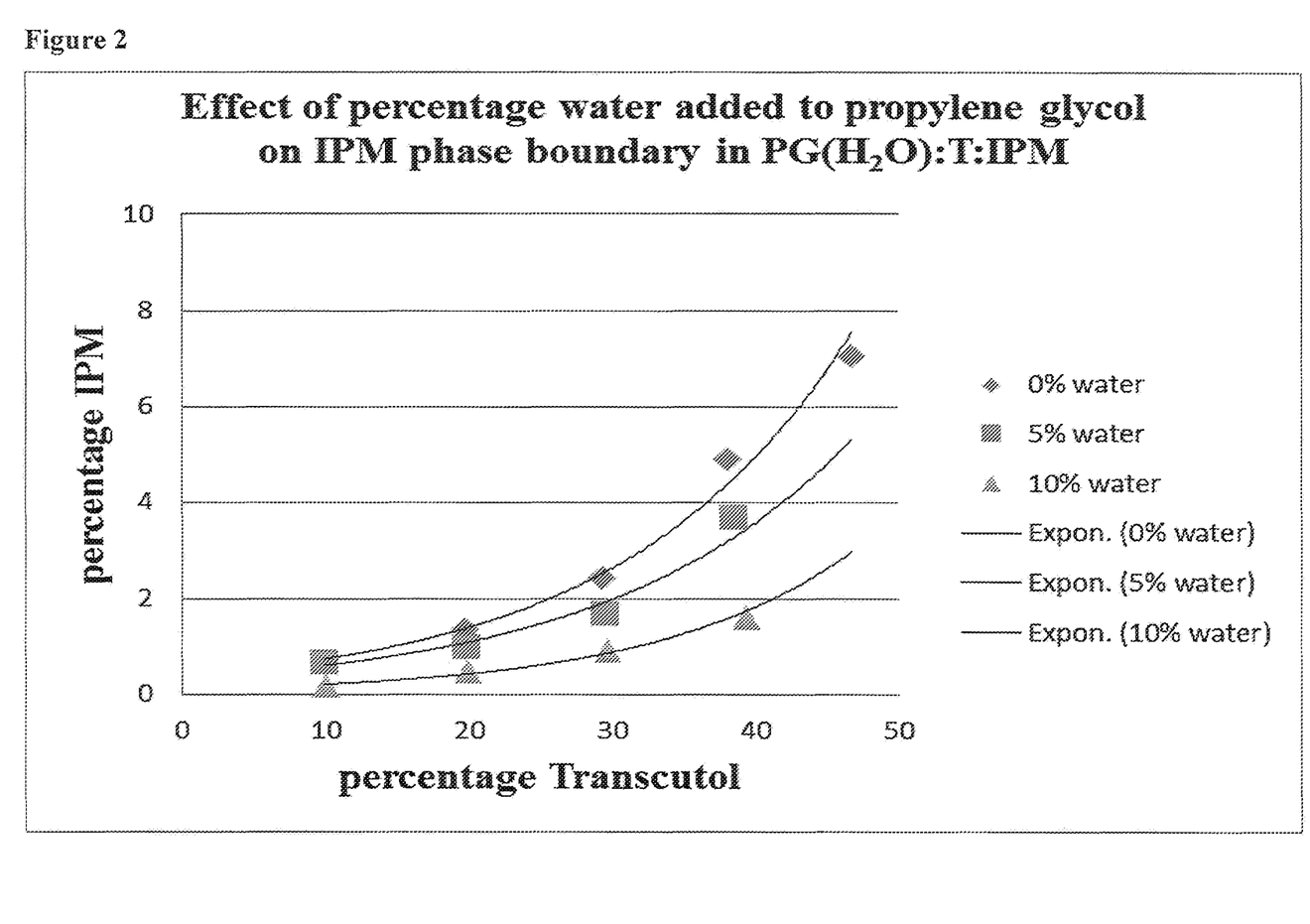
FIG. 2 is a graph showing the effect on the phase boundary of FIG. 1 of addition of water.

Referring to FIG. 2, it can be seen how the presence of water at 5% and 10% based on propylene glycol reduces the amount of isopropyl myristate which can be tolerated for a single-phase system.

In terms of the concentration of NSAID in the composition, it is desirable to provide a dose level sufficient to sustain the percutaneous absorption process and to achieve therapeutic tissue levels at the target site resulting in inhibitory concentrations in the range $IC_{90-99}$. Taking account of steady state plasma levels, ibuprofen clearance rates and the area over which a topical formulation is typically applied, compositions according to the present invention can be formulated to provide a target in vivo flux of between 5 and 25, preferably 10-20, $\mu g/cm^2/hr$ which, assuming a twice daily (12 hours) dosing regime, requires a concentration of ibuprofen of around 2.5% by weight, within a broader range of from 0.5 to 5% by weight. Alternatively, the ibuprofen may be in a range of 0.5 to 2.5%, such as 0.5 to 1.5%, by weight relative to the total weight of the composition.

Overall, to provide a saturation level of ibuprofen in the range of approximately 0.5% to 5.0% concentration by weight, and to optimize the glycol and polar lipid component, it is preferred to employ carrier systems on or close to the phase boundary and relatively rich in glycol, that is, those systems which lie in the upper part of the phase diagram of FIG. 1.

In order to predict in vivo rates of human skin penetration, in vitro experiments are generally used, since there is an established correlation between in vitro and in vivo performance. Systems such as shown in FIG. 1 have been found to provide optimised levels of flux across human skin, and very significant enhancement of flux compared with Voltarol as control.

In the examples described below, all ingredients comply with the requirements and standards of the US Pharmacopeia (USP), which also applies as appropriate elsewhere throughout this specification and claims.

The following Tables provide examples of various formulations according to the invention, bearing in mind that the preferred polyhydric alcohol is propylene glycol, the preferred glycol ether is Transcutol and the preferred ester is isopropyl myristate.

Table 1 shows formulations having alternative polyhydric alcohols;

Table 2 shows formulations having alternative glycol ethers;

Table 3 shows formulations having alternative esters;

Table 4 shows water-containing gel formulations at different pH values using liquid ammonia;

Table 5 shows non-aqueous gel formulations at different pH values using liquid ammonia; and Table 6 shows non-aqueous gel formulations neutralised either by liquid ammonia or by diethylamine.

TABLE 1

Composition of formulations containing alternative polyhydric alcohols

| | | TIB formulation compositions (% w/w) - pH 7 | |
|---|---|---|---|
| Excipient | Excipient type | TIB005 - PHA 2 | TIB005 - PHA 3 |
| Ibuprofen | API | 10.00 | 10.00 |
| Propylene glycol | Polyhydric alcohols | 32.79 | 10.79 |
| Glycerol | | — | 20.00 |
| Dipropylene glycol | | 10.00 | — |
| Hexylene glycol | | — | 12.00 |
| Transcutol P | Glycol ethers | 19.72 | 19.72 |
| Isopropyl myristate | Ester | 2.47 | 2.47 |
| Dimethicone (0.65 CST) | Solvent/skin conditioner | 1.50 | 1.50 |
| 1st IPA | Volatile solvent | 15.00 | 15.00 |
| HPC HF | Gelling agent | 1.00 | 1.00 |
| Liquid ammonia | Neutralising agent | to pH 7 | to pH 7 |
| 2nd IPA | Volatile solvent | q.s. 100% | q.s. 100% |

(—) not included

TABLE 2

Composition of formulations containing alternative glycol ethers

| | | TIB formulation compositions (% w/w) - pH 7 | | | |
|---|---|---|---|---|---|
| Excipient | Excipient type | TIB005 - GE 1 | TIB005 - GE 3 | TIB005 - GE 4 | TIB005 - GE 7 |
| Ibuprofen | API | 10.00 | 10.00 | 10.00 | 10.00 |
| Propylene glycol | Polyhydric alcohol | 42.79 | 42.79 | 42.79 | 52.65 |
| Transcutol P | Glycol ether | 18.72 | — | 10.00 | — |
| Phenoxyethanol | | 1.00 | — | — | — |
| Diethylene glycol monomethyl ether | | — | 19.72 | — | — |
| Arlamol PS15 | | — | — | 9.72 | — |
| Isopropyl myristate | Ester | 2.47 | 2.47 | 2.47 | 2.47 |
| Dimethicone (0.65 CST) | Solvent/skin conditioner | 1.50 | 1.50 | 1.50 | 1.50 |
| 1st IPA | Volatile solvent | 15.00 | 15.00 | 15.00 | 24.86 |
| HPC HF | Gelling agent | 1.00 | 1.00 | 1.00 | 1.00 |
| Liquid ammonia | Neutralising agent | to pH 7 | to pH 7 | to pH 7 | to pH 7 |
| 2nd IPA | Volatile solvent | q.s. 100% | q.s. 100% | q.s. 100% | q.s. 100% |

(—) not included

TABLE 3

Compositions of formulations containing alternative esters

| | | TIB formulation compositions (% w/w) - pH 7 | | |
|---|---|---|---|---|
| Excipient | Excipient type | TIB005-FAE 1 | TIB005-FAE 2 | TIB005-FAE 4 |
| Ibuprofen | API | 10.00 | 10.00 | 10.00 |
| Propylene glycol | Polyhydric alcohol | 42.79 | 42.79 | 42.79 |
| Transcutol P | Glycol ether | 19.72 | 19.72 | 19.72 |
| Isopropyl palmitate | Esters | 2.47 | — | — |
| Miglyol 812 | | — | 2.47 | — |
| Glyceryl Stearate (GMS) | | — | — | — |
| Labrafil ® M1944CS | | — | — | 2.47 |
| Dimethicone (0.65 CST) | Solvent/skin conditioner | 1.50 | 1.50 | 1.50 |
| 1st IPA | Volatile solvent | 15.00 | 15.00 | 15.00 |
| HPC HF | Gelling agent | 1.00 | 1.00 | 1.00 |
| Liquid ammonia | Neutralising agent | to pH 7 | to pH 7 | to pH 7 |
| 2nd IPA | Volatile solvent | q.s. 100% | q.s. 100% | q.s. 100% |

(—) not included

TABLE 4

TIB based ibuprofen gels containing 5% water at pH 4-7.

| | TIB formulation compositions (% w/w) | | | |
|---|---|---|---|---|
| Excipient | TIB003 AQ - pH 4 | TIB003 AQ - pH 5 | TIB003 AQ - pH 6 | TIB003 AQ- pH 7 |
| Ibuprofen | 10.00 | 10.00 | 10.00 | 10.00 |
| Propylene glycol | 42.79 | 42.79 | 42.79 | 42.79 |
| Transcutol P | 19.72 | 19.72 | 19.72 | 19.72 |
| Isopropyl myristate | 2.47 | 2.47 | 2.47 | 2.47 |
| Dimethicone (0.65 CST) | 1.50 | 1.50 | 1.50 | 1.50 |
| 1st IPA | 15.00 | 15.00 | 15.00 | 15.00 |
| Water | 5.00 | 5.00 | 5.00 | 5.00 |
| HPC HF | 1.00 | 1.00 | 1.00 | 1.00 |
| Liquid ammonia | to pH 4 | to pH 5 | to pH 6 | to pH 7 |
| 2nd IPA | q.s. 100% | q.s. 100% | q.s. 100% | q.s. 100% |

Similar formulations have been prepared including water partially or fully replacing IPA, as follows: (i) 0% water; (ii)

50:50 IPA:water; and (iii) 0% IPA, using diethylamine as the neutralising agent. All formed clear gels.

TABLE 5

TIB based ibuprofen gels containing no water at pH 4-7*.

TIB formulation compositions (% w/w)

| Excipient | TIB003 non-AQ pH 4 | TIB003 non-AQ pH 5 | TIB003 non-AQ pH 6 | TIB003 non-AQ pH 7 (TIB003 liquid ammonia) |
|---|---|---|---|---|
| Ibuprofen | 10.00 | 10.00 | 10.00 | 10.00 |
| Propylene glycol | 42.79 | 42.79 | 42.79 | 42.79 |
| Transcutol P | 19.72 | 19.72 | 19.72 | 19.72 |
| Isopropyl myristate | 2.47 | 2.47 | 2.47 | 2.47 |
| Dimethicone (0.65 CST) | 1.50 | 1.50 | 1.50 | 1.50 |
| 1st IPA | 15.00 | 15.00 | 15.00 | 15.00 |
| HPC HF | 1.00 | 1.00 | 1.00 | 1.00 |
| Liquid ammonia | to pH 4 | to pH 5 | to pH 6 | to pH 7 |
| 2nd IPA | q.s. 100% | q.s. 100% | q.s. 100% | q.s. 100% |

*TIB003 non-AQ pH 7 is the same formulation as the TIB003 liquid ammonia, formulation column 2, table 6.

TABLE 6

TIB based ibuprofen gels containing liquid ammonia or diethylamine.

TIB formulation compositions (% w/w) - pH 7

| Excipient | TIB003 Liquid ammonia 5% | TIB003 Liquid ammonia 10% | TIB003 LA w/o dimethicone | TIB003 Diethylamine 5%/10% | TIB003 DE w/o dimethicone |
|---|---|---|---|---|---|
| Ibuprofen | 5.00 | 10.00 | 10.00 | 5.00 or 10.00 | 10.00 |
| Propylene glycol | 42.79 | 42.79 | 42.79 | 42.79 | 42.79 |
| Transcutol P | 19.72 | 19.72 | 19.72 | 19.72 | 19.72 |
| Isopropyl myristate | 2.47 | 2.47 | 2.47 | 2.47 | 2.47 |
| Dimethicone (0.65 CST) | 1.50 | 1.50 | — | 1.50 | — |
| 1st IPA | 15.00 | 15.00 | 15.00 | 15.00 | 15.00 |
| Water | — | — | — | — | — |
| HPC HF | 1.00 | 1.00 | 1.00 | 1.00 | 1.00 |
| Liquid ammonia | to pH 7 | to pH 7 | to pH 7 | — | — |
| Diethylamine | — | — | — | to pH 7 | to pH 7 |

(—) not included

The following compositions according to the invention were subject to permeation experiments compared with formulations according to WO2012/151427 (Aponia Laboratories), according to the following conditions:

Franz cell size—small (average surface area and volume of approximately 0.6 cm$^2$ and 2 mL, respectively)
Water bath temperature: 37° C.
Sampling volume—200 μL
Receiver fluid—2.0% BriJ in 20:80 Ethanol:PBS
Timepoints: t=0, 1, 2, 4, 6, 24 and 30 hr

TABLE 7

Compositions of formulations containing ibuprofen tested in the full scale permeation experiment.

| Excipient | APONIA 2 | APONIA 3 | APONIA 10 | TIB003 diethylamine | TIB003 Liquid ammonia | TIB003 AQ pH 4 |
|---|---|---|---|---|---|---|
| Ibuprofen | 10.00 | 10.00 | 10.00 | 10.00 | 10.00 | 10.00 |
| Propylene glycol | 20.00 | 10.00 | 10.00 | 42.79 | 42.79 | 42.79 |
| Transcutol P | 25.00 | 10.00 | 25.00 | 19.72 | 19.72 | 19.72 |
| Isopropyl myristate | 5.00 | 5.00 | 5.00 | 2.47 | 2.47 | 2.47 |
| Tween 20 | — | 2.00 | — | — | — | — |
| Benzyl alcohol | — | 5.00 | — | — | — | — |
| Water | 10.00 | 10.00 | — | — | — | 5.00 |
| HPC | 2.00 | 2.00 | 2.00 | — | — | — |
| IPA | 28.00 | 46.00 | — | 15.00 | 15.00 | 15.00 |

TABLE 7-continued

Compositions of formulations containing ibuprofen tested in the full scale permeation experiment.

| Excipient | APONIA 2 | APONIA 3 | APONIA 10 | TIB003 diethylamine | TIB003 Liquid ammonia | TIB003 AQ pH 4 |
|---|---|---|---|---|---|---|
| Ethanol | — | — | 48.00 | — | — | — |
| Dimethicone (0.65 CST) | — | — | — | 1.50 | 1.50 | 1.50 |
| Liquid ammonia | — | — | — | — | to pH 7 | to pH 4 |
| Diethylamine | — | — | — | to pH 7 | — | — |
| Total | 100.00 | 100.00 | 100.00 | 100.00 | 100.00 | 100.00 |

Figure 3:
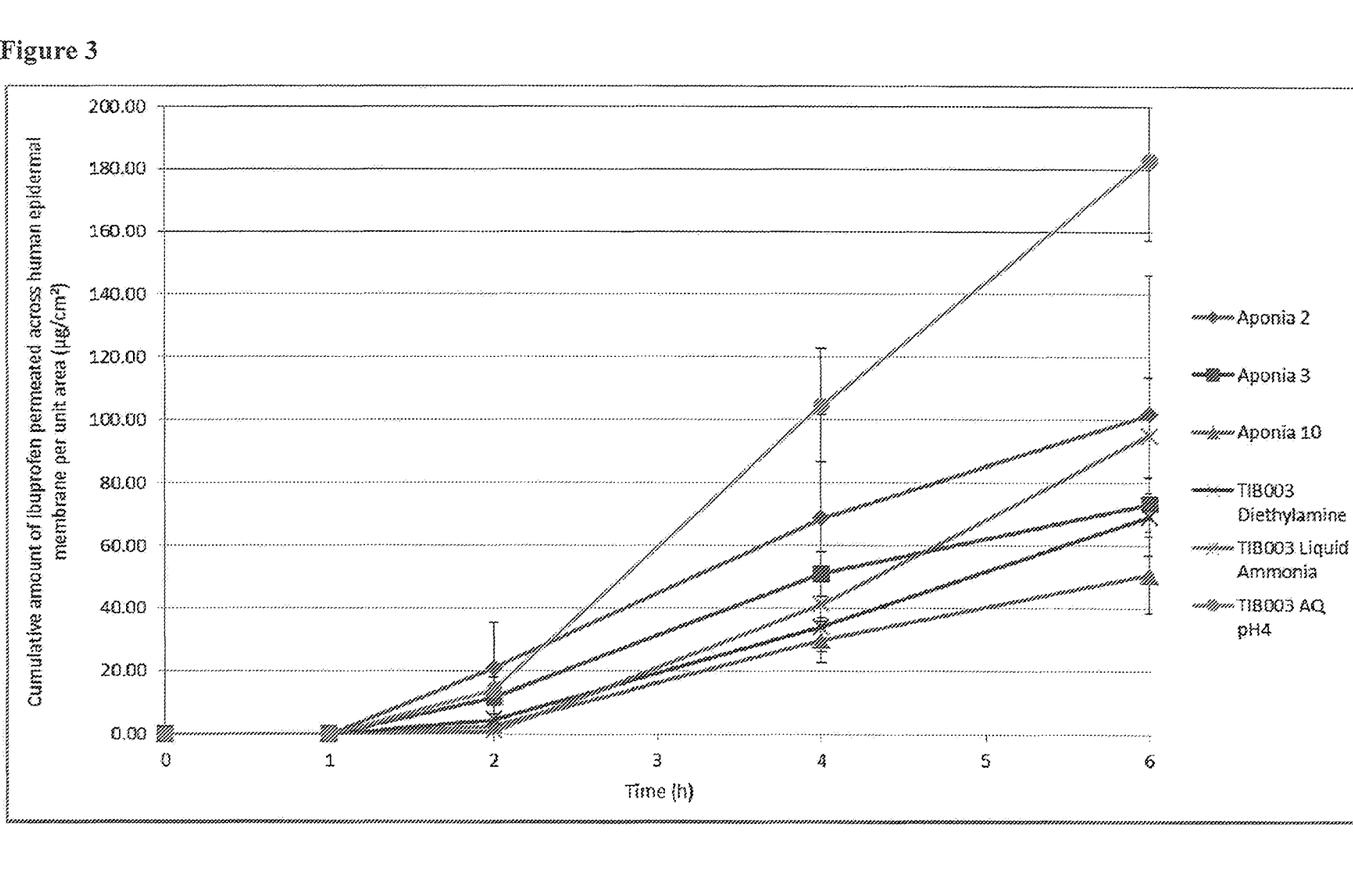
FIG. 3 is a graph showing skin permeation of ibuprofen for a range of gels shown in Table 7, including examples according to the invention and comparative gels, over 6 hours.
Figure 4:
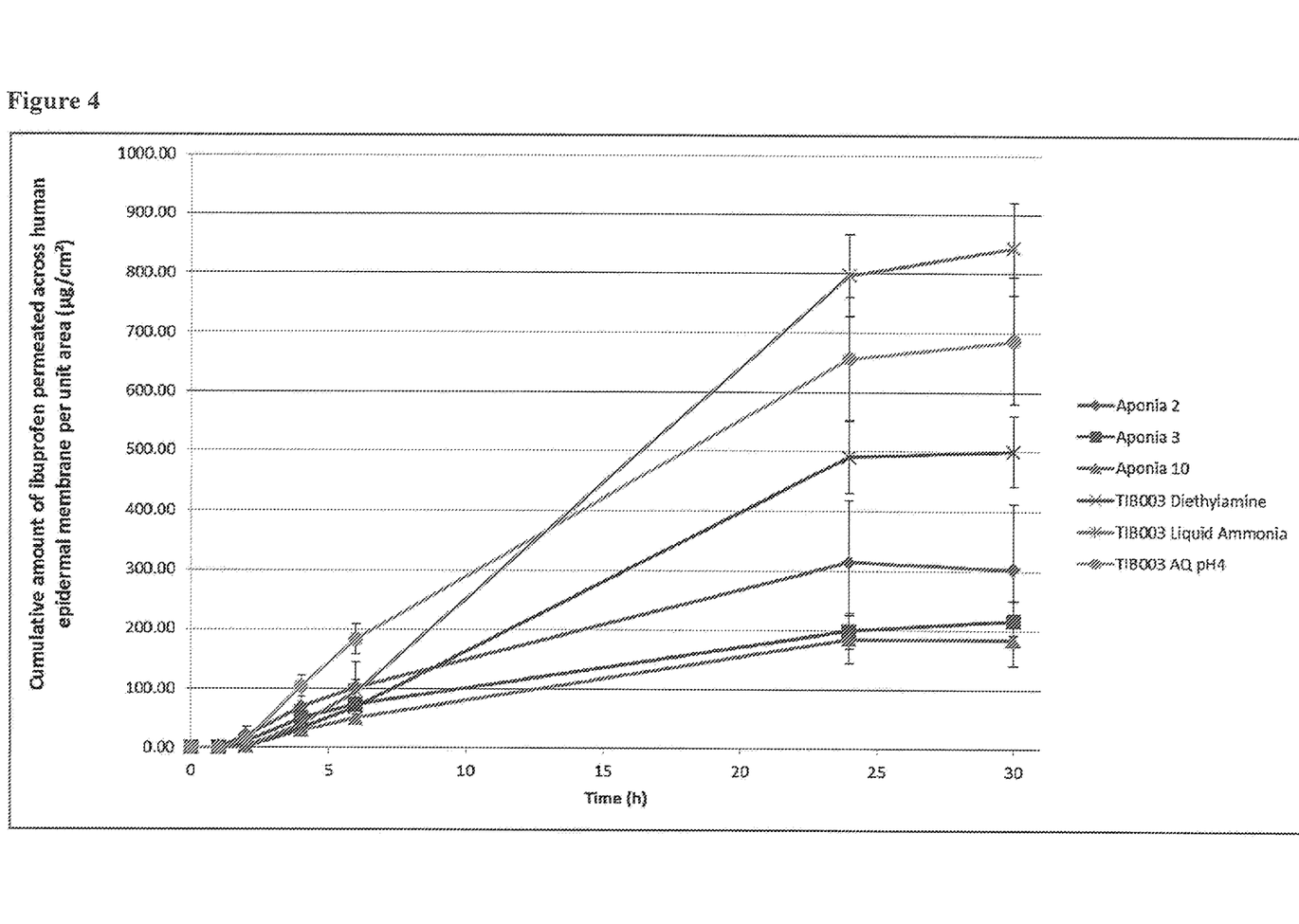
FIG. 4 is a graph showing skin permeation over 30 hours for the gels of FIG. 3.
Figure 5:
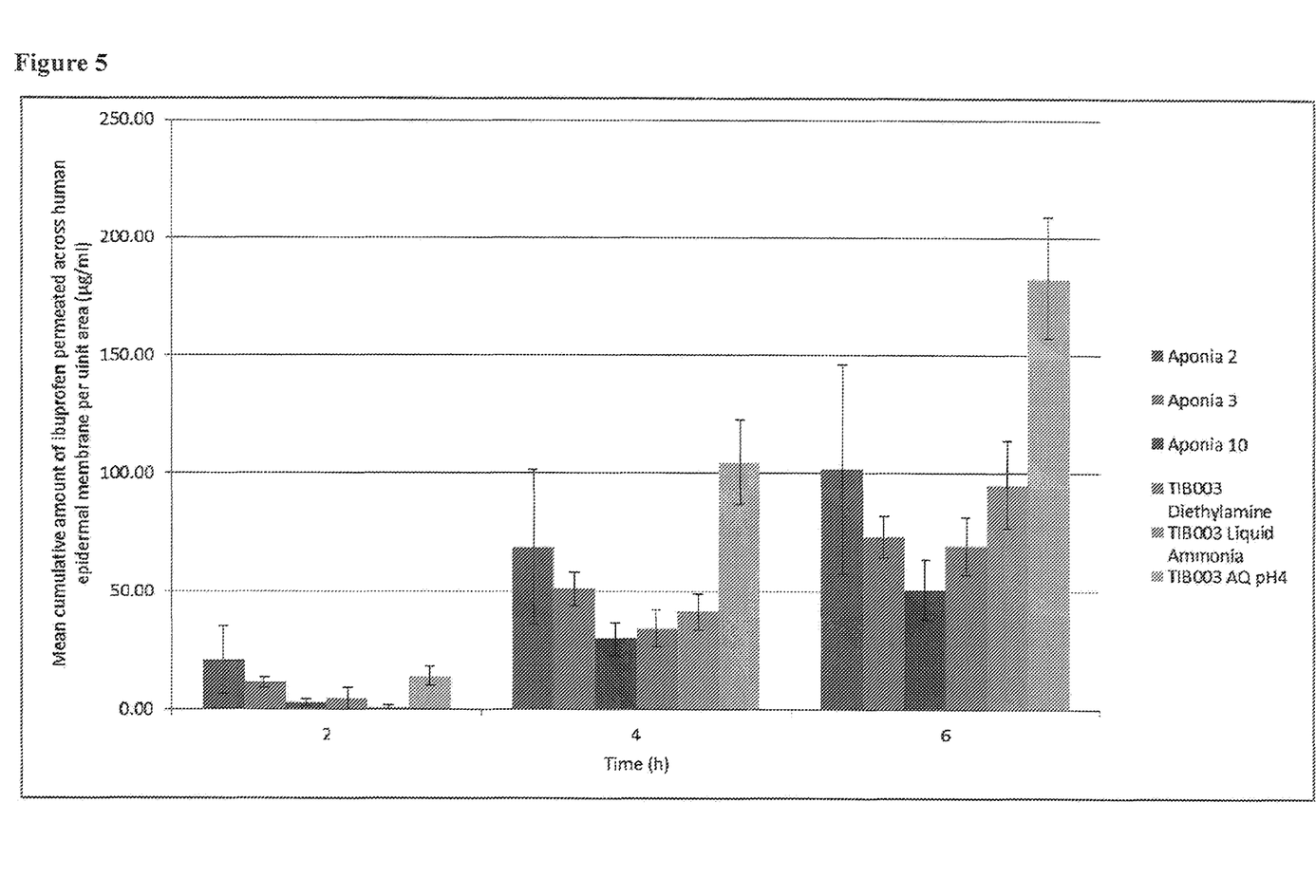
FIG. 5 is a histogram showing mean amounts of ibuprofen at 2, 4 and 6 hours, using the gels of FIGS. 3 and 4.

Permeation results for the compositions of Table 7 are shown in the accompanying FIGS. 3, 4 and 5, of which:

FIG. 3 shows the mean cumulative amount of ibuprofen permeated across epidermal membrane over 6 hours;

FIG. 4 shows the mean cumulative amount as in FIG. 3 but over 30 hours; and

FIG. 5 shows the mean cumulative amount of ibuprofen permeated per unit area across epidermal membrane from various gels at 2, 4 and 6 hours.

Table 8 shows the average flux and percentage of applied dose of ibuprofen permeated across human epidermal membrane from the formulations of Table 7.

TABLE 8

Average flux and percentage of applied dose of ibuprofen permeated across human epidermal membrane from a range of formulations. Calculated from t = 2 to 6 h, each point represents mean ± SEM (n = 5-6)

| Formulation | Flux over 2-6 h (μg/cm²/h) | % of applied dose permeated at t = 6 h | % of applied dose permeated at t = 30 h |
|---|---|---|---|
| Aponia 2 | 20.22 ± 7.74 | 15.42 ± 6.41 | 33.54 ± 9.34 |
| Aponia 3 | 15.47 ± 2.01 | 6.42 ± 0.57 | 19.04 ± 2.66 |
| Aponia 10 | 11.99 ± 6.92 | 4.14 ± 0.80 | 15.30 ± 2.70 |
| TIB003 diethylamine | 16.17 ± 2.56 | 6.27 ± 1.16 | 44.56 ± 4.62 |
| TIB003 liquid ammonia | 23.56 ± 4.41 | 8.38 ± 1.38 | 74.53 ± 4.63 |
| TIB003 AQ pH 4 | 42.23 ± 5.68 | 16.40 ± 2.46 | 60.97 ± 9.19 |

The results illustrate that compositions according to the invention generally demonstrate superior results to the Aponia compositions especially at t=4 and above and in particular that the composition at pH 4 with liquid ammonia as the neutralizing agent gives superior results even at t=2.

Further in vitro permeation tests were carried out on more compositions according to the invention using three skin donors. Conditions for the permeation experiment were as follows:

Franz cell size—small cells (average surface area and volume of approximately 0.6 cm² and 2 mL, respectively)

Water bath temperature: 37° C.

Sampling volume—200 μL

Receiver fluid—2.0% BriJ in 20:80 Ethanol:PBS

Timepoints: t=0, 1, 2, 4, 6, 8, 10, 12 and 24 hr

Dosing amounts—5 mg/cm²

TABLE 9

Composition of formulations containing ibuprofen for the in vitro permeation experiment

| | Theoretical composition (% w/w) | | |
|---|---|---|---|
| Excipient | TIB003 DE pH 7 | TIB003 DE pH4 | Uber TIB |
| Ibuprofen | 10 | 10 | 10 |
| Propylene glycol | 42.79 | 42.79 | 55.04 |
| Transcutol P | 19.72 | 19.72 | 9.87 |
| Isopropyl myristate | 2.47 | 2.47 | 0.89 |
| Water | — | — | 5 |
| HPC | 1 | 1 | 1 |
| IPA 1st addition | 15 | 15 | 15 |
| Dimethicone (0.65 CST) | 1.5 | 1.5 | 1.5 |
| Liquid ammonia | — | — | to pH 7 |
| Diethylamine | to pH 7 | to pH4 | — |
| IPA 2nd addition | Add required amount based on weight to give 100% | | |

Figure 6:
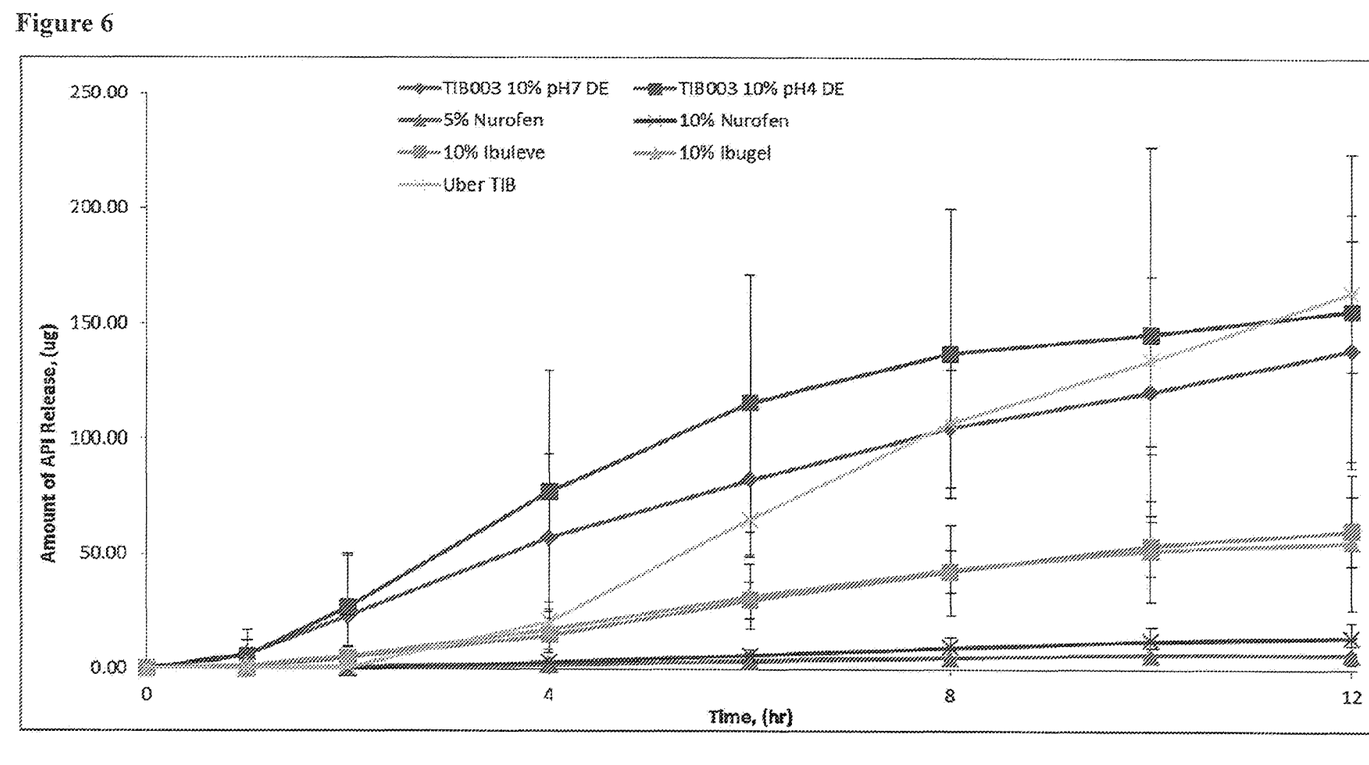
FIG. 6 is a graph showing skin penetration of ibuprofen for a range of gels shown in Table 9, including examples according to the invention and comparative gels, over 12 hours.
Figure 7:
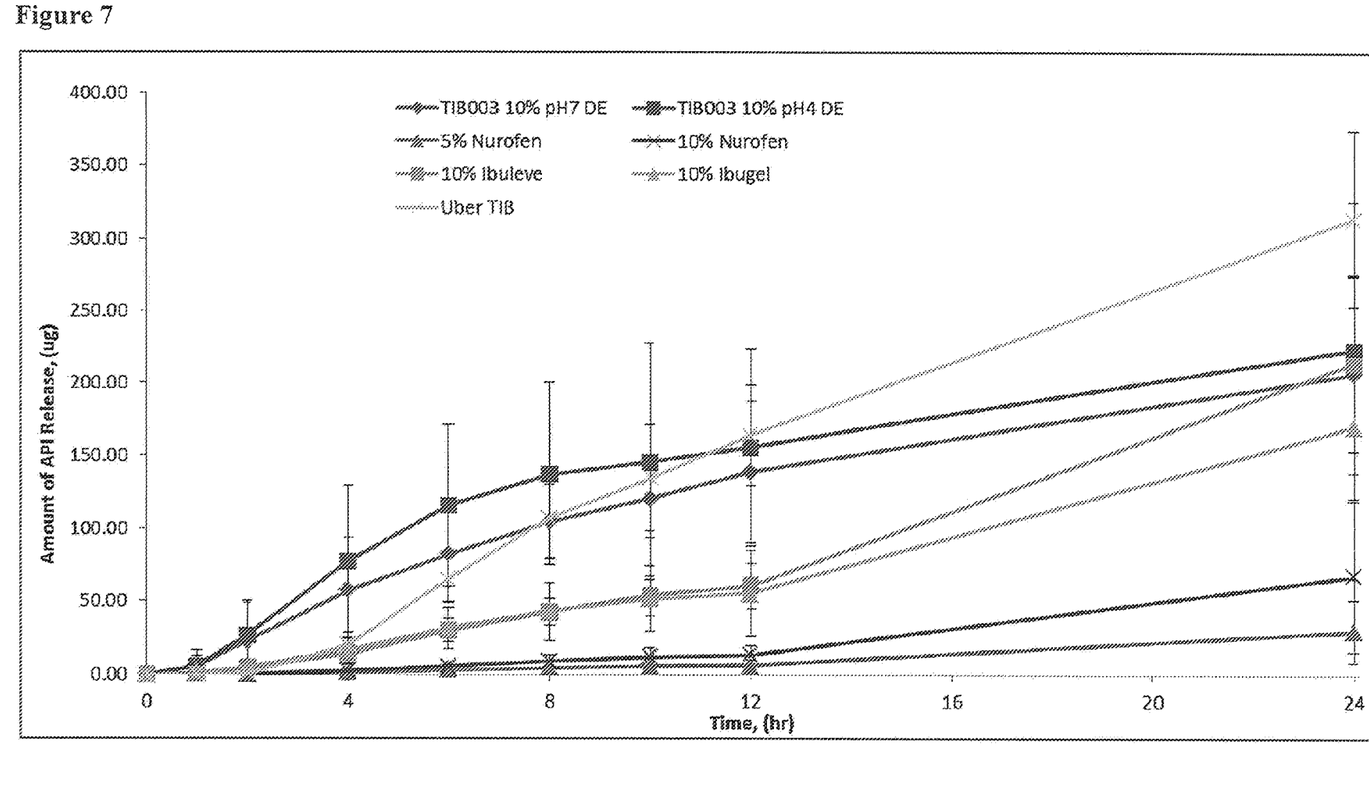
FIG. 7 is a graph showing skin penetration over 24 hours for the gels of FIG. 6.
Figure 8:
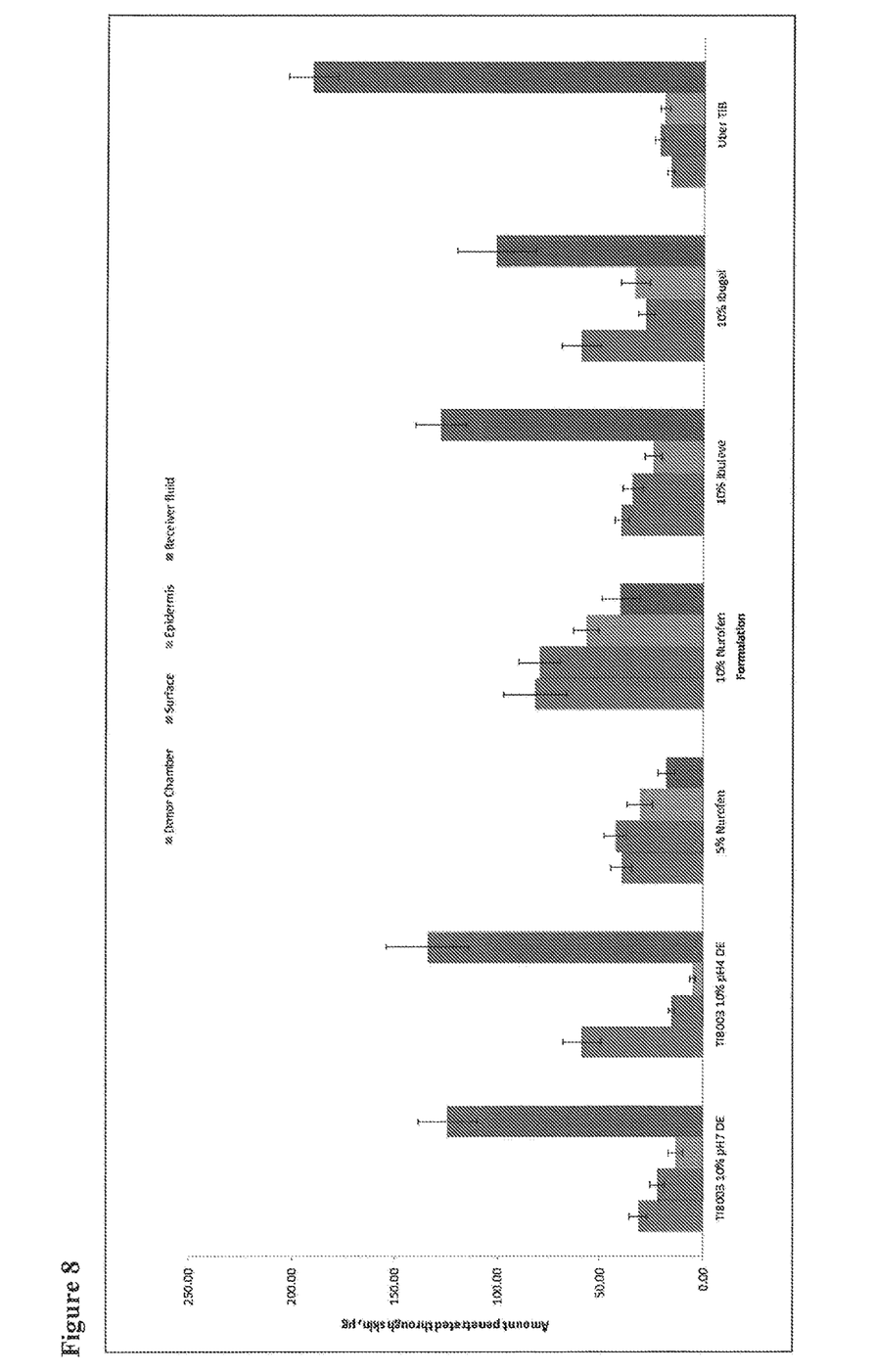
FIG. 8 is a histogram showing the amounts of ibuprofen recovered from the donor chamber, skin surface, epidermal skin layer and receiver fluid of a Franz cell apparatus in the skin penetration experiments of FIGS. 6 and 7.

The results are shown in the accompanying FIGS. 6 to 8, in which FIG. 6 illustrates the amount of API penetration per unit area for a range of gels over 12 hours, where the comparative formulations were 5% Nurofen, 10% Nurofen, 10% Ibuleve and 10% Ibugel. FIG. 7 is similar but the time period is 24 hours, and FIG. 8 shows the mean cumulative amounts of ibuprofen recovered respectively from the donor chamber, skin surface, epidermal skin layer and receiver fluid following application of the same range of gels over 24 hours.

It can readily be observed from FIG. 8 that all TIB compositions gave excellent results in terms of the amount of ibuprofen in the receiver fluid with only relatively small amounts retained in the other locations and from FIGS. 6 and 7 that penetration rates are superior from the outset for the TIB003 compositions and onwards to t=24, while Uber TIB has an initial time lag until t=4, after which it recovers rapidly and from t=12 is superior to all other compositions up to t=24. The initial time lag may be attributed to initial delay in evaporation of ammonia, thus maintaining the pH closer to pH7 for the period immediately following application. For use in vivo, penetration is likely to be faster because the film is thinner and is exposed to air currents rather than, in vitro, being a thicker film in a funnel-protected atmosphere. Additionally, in vivo, the pretreatment wash would be likely to remove the acid mantle, enhancing skin penetration generally. The enhanced rate from t=4 is attributable to the higher concentration of propylene glycol, resulting in higher ibuprofen thermodynamic activity.

The results above are also shown in the following Table 10. Again, the percentage of the applied dose permeated at the various time points for the TIB compositions, compared with the non-inventive compositions, is immediately apparent.

TABLE 10

Average flux and percentage of applied dose of ibuprofen permeated across human epidermal membrane from a range of formulations. Calculated from t = 1 to 6 h, each point represents mean ± SEM, n = 8-12 total (2-4 per donor)

| Formulation | Flux over 1-6 h ($\mu g/cm^2/h$) | % of applied dose permeated at t = 6 h | % of applied dose permeated at t = 24 h |
|---|---|---|---|
| TIB003 10% pH7 DE | 13.93 ± 1.67 | 15.69 ± 2.31 | 41.68 ± 4.91 |
| TIB003 10% pH4 DE | 21.85 ± 3.00 | 23.77 ± 3.82 | 45.84 ± 7.14 |
| D1 5% Nurofen | 0.82 ± 0.25 | 1.31 ± 0.44 | 11.96 ± 2.80 |
| D1 10% Nurofen | 1.13 ± 0.18 | 1.07 ± 0.17 | 12.87 ± 3.01 |
| D1 10% Ibuleve | 5.82 ± 0.54 | 6.10 ± 0.70k | 43.34 ± 4.00 |
| D1 10% Ibugel | 6.07 ± 0.76 | 6.12 ± 0.83 | 32.94 ± 5.82 |
| Uber TIB 10% | 13.07 ± 1.13 | 12.75 ± 1.09 | 62.34 ± 4.65 |
| Uber TIB 10%* | 19.23 ± 1.98* | N/A | N/A |

*Flux calculated over t = 4-10 h period.

The invention claimed is:

1. A topical composition for application of an NSAID comprising ibuprofen, the composition comprising a solution or suspension of the NSAID as active ingredient in a residual carrier system comprising a polyhydric alcohol, a glycol ether, an alkyl ester of a $C_{10}$ to $C_{20}$ fatty acid and optionally water, the ingredients of the residual carrier system having the following concentrations in percentages by weight:
   polyhydric alcohol 50-90
   glycol ether 7.5-40
   alkyl ester of a $C_{10}$ to $C_{20}$ fatty acid 0.5-5
   water 0-20
in which either the composition or a residual phase formed by the residual carrier system is in a single phase under ambient conditions, wherein the NSAID is supersaturated in the residual phase, and
   wherein the composition includes a volatile neutralizing agent and has a pH of 6 to 8 before application to the skin.

2. A composition according to claim 1, in which the neutralizing agent is water-miscible.

3. A composition according to claim 1, wherein in use and on application to the skin, the volatile neutralizing agent evaporates to cause the pH of the composition to decrease to 5 or less.

4. A composition according to claim 1, in which the polyhydric alcohol is a glycol.

5. A composition according to claim 1, in which the alkyl ester of a $C_{10}$ to $C_{20}$ fatty acid comprises a branched-chain alkyl ester of a $C_{10}$ to $C_{20}$ saturated carboxylic acid.

6. A composition according to claim 1, in which the glycol ether is a diethylene glycol ether.

7. A composition according to claim 1, in which the percentage by weight ranges for the ingredients are as follows:

| | |
|---|---|
| polyhydric alcohol | 50-80 |
| glycol ether | 15-35 |
| alkyl ester of a $C_{10}$ to $C_{20}$ fatty acid | 1-5 |
| water | 2.5-20. |

8. A composition according to claim 1, in which the percentage by weight ranges for the ingredients are as follows:

| | |
|---|---|
| polyhydric alcohol | 55-70 |
| glycol ether | 25-35 |
| alkyl ester of a $C_{10}$ to $C_{20}$ fatty acid | 2.5-5 |
| water | 5-15. |

9. A composition according to claim 1, in which the percentage by weight ranges for the ingredients are as follows:

| | |
|---|---|
| polyhydric alcohol | 60-65 |
| glycol ether | 25-30 |
| alkyl ester of a $C_{10}$ to $C_{20}$ fatty acid | 2.5-4 |
| water | 5-10. |

10. A composition according to claim 1, further comprising a volatile solvent.

11. A composition according to claim 10, in which the volatile solvent is a lower alcohol containing up to 5 carbon atoms or a liquid-phase ketone.

12. A composition according to claim 11, in which the volatile solvent is ethanol or isopropyl alcohol (WA).

13. A composition according to claim 10, in which the volatile solvent is in a range of 15 to 40% by weight relative to the total weight of the composition.

14. A composition according to claim 1, further comprising a polyhydric alcohol including three or more hydroxyl groups as part of the residual carrier system.

15. A composition according to claim 14, in which the polyhydric alcohol including three or more hydroxyl groups is glycerol or sorbitol.

16. A composition according to claim 1, comprising, in total formulation terms, in percentages by weight and apart from the NSAID:

| | |
|---|---|
| polyhydric alcohol | 20-60 |
| glycol ether | 5-30 |
| alkyl ester of a $C_{10}$ to $C_{20}$ fatty acid | 0.3-3 |
| water if added | 2.5-15 |
| lower alcohol | 20-50. |

17. A composition according to claim 16, comprising, in total formulation terms, in percentages by weight:

| | |
|---|---|
| NSAID | 0.5-5% |
| polyhydric alcohol | 25-50 |
| glycol ether | 10-25 |
| alkyl ester of a $C_{10}$ to $C_{20}$ fatty acid | 1-2.5 |
| water if added | 2.5-10 |
| lower alcohol | 20-50. |

18. A method of relieving pain and/or inflammation, the method comprising topically applying an effective amount of the composition of claim 1 to the skin of a patient.

19. A composition according to claim 1, in which the polyhydric alcohol is propylene glycol, the alkyl ester of a $C_{10}$ to $C_{20}$ fatty acid is isopropyl myristate, and/or the glycol ether is diethylene glycol monoethyl ether (Transcutol®).

* * * * *

UNITED STATES PATENT AND TRADEMARK OFFICE
CERTIFICATE OF CORRECTION

PATENT NO. : 11,376,213 B2
APPLICATION NO. : 16/308032
DATED : July 5, 2022
INVENTOR(S) : Adrian Davis and Marc Barry Brown It is certified that error appears in the above-identified patent and that said Letters Patent is hereby corrected as shown below:

In the Claims

Claim 12, Column 18, Line 27, delete "(WA)" and insert --(IPA)--

Signed and Sealed this
Eighth Day of November, 2022

Katherine Kelly Vidal
*Director of the United States Patent and Trademark Office*